(12) United States Patent
Saylor et al.

(10) Patent No.: US 10,299,802 B2
(45) Date of Patent: May 28, 2019

(54) DRILL PIN FOR FIXATION OF LIGAMENTS USING BUTTON/LOOP CONSTRUCT

(71) Applicant: Arthrex, Inc., Naples, FL (US)

(72) Inventors: James Saylor, Clovis, CA (US); Jonathan Decker, Wellsville, UT (US)

(73) Assignee: ARTHREX, INC., Naples, FL (US)

(*) Notice: Subject to any disclaimer, the term of this patent is extended or adjusted under 35 U.S.C. 154(b) by 161 days.

(21) Appl. No.: 14/536,205

(22) Filed: Nov. 7, 2014

(65) Prior Publication Data
US 2015/0133941 A1    May 14, 2015

Related U.S. Application Data

(60) Division of application No. 12/010,537, filed on Jan. 25, 2008, now Pat. No. 8,882,833, which is a
(Continued)

(51) Int. Cl.
*A61B 17/16* (2006.01)
*A61B 17/04* (2006.01)
(Continued)

(52) U.S. Cl.
CPC ...... *A61B 17/1615* (2013.01); *A61B 17/0401* (2013.01); *A61B 17/1675* (2013.01);
(Continued)

(58) Field of Classification Search
CPC ............ A61B 17/1615; A61B 17/1617; A61B 17/1635; A61B 17/1675; A61B 17/1682;
(Continued)

(56) References Cited

U.S. PATENT DOCUMENTS 2,543,206 A * 2/1951 Smith .................... B27G 15/00
                                                          408/224
2,689,131 A * 9/1954 Priest .................... B27G 15/00
                                                          144/241
(Continued)

FOREIGN PATENT DOCUMENTS

EP    0 495 487 A2    7/1992
EP    0 556 570 A1    8/1993
(Continued)

OTHER PUBLICATIONS

Albee, "Bone Surgery with Machine Tools," Scientific American, Apr. 1936, pp. 178-181.*
(Continued)

*Primary Examiner* — Matthew J Lawson
*Assistant Examiner* — Amy R Sipp
(74) *Attorney, Agent, or Firm* — Carlson, Gaskey & Olds

(57) ABSTRACT

A reconstruction system for ligament employing a button/loop construct with a drill pin. The drill pin has a shaft with a proximal and a distal end. A pin tip provided at the distal end of the shaft has a width greater than the shaft diameter. The pin tip helps cut a wider tunnel for fixation of ligaments/grafts in reconstructive surgeries. The shaft of the drill pin is provided with a laser marks for measurement of intraosseous length.

17 Claims, 19 Drawing Sheets

Related U.S. Application Data continuation-in-part of application No. 11/889,740, filed on Aug. 16, 2007, now Pat. No. 9,101,461.

(60) Provisional application No. 60/897,230, filed on Jan. 25, 2007, provisional application No. 60/837,937, filed on Aug. 16, 2006.

(51) Int. Cl.
*A61F 2/08* (2006.01)
*A61B 17/17* (2006.01)
*A61B 90/00* (2016.01)

(52) U.S. Cl.
CPC ........ *A61B 17/1764* (2013.01); *A61F 2/0805* (2013.01); *A61F 2/0811* (2013.01); *A61B 17/1714* (2013.01); *A61B 17/1796* (2013.01); *A61B 2017/0404* (2013.01); *A61B 2017/0414* (2013.01); *A61B 2090/062* (2016.02); *A61F 2002/0852* (2013.01); *A61F 2002/0882* (2013.01)

(58) Field of Classification Search
CPC ............ A61B 17/1686; A61B 17/1714; A61B 17/1764; A61B 17/1796; A61B 17/1697
See application file for complete search history.

(56) References Cited

U.S. PATENT DOCUMENTS

| | | | |
|---|---|---|---|
| 5,055,105 A | 10/1991 | Hamlin et al. | |
| 5,098,435 A | 3/1992 | Stednitz et al. | |
| 5,211,647 A | 5/1993 | Schmieding | |
| 5,257,996 A * | 11/1993 | McGuire | A61B 17/15 606/104 |
| 5,306,301 A * | 4/1994 | Graf | A61B 17/0401 606/151 |
| 5,320,115 A | 6/1994 | Kenna | |
| 5,320,626 A | 6/1994 | Schmieding | |
| 5,370,662 A | 12/1994 | Stone et al. | |
| 5,549,613 A * | 8/1996 | Goble | A61B 17/1617 408/231 |
| 5,645,588 A | 7/1997 | Graf et al. | |
| 5,649,796 A * | 7/1997 | Durney | B27G 15/00 408/144 |
| 5,697,738 A * | 12/1997 | Stone | B21J 5/12 408/225 |
| 5,713,905 A | 2/1998 | Goble et al. | |
| 6,015,411 A | 1/2000 | Ohkoshi et al. | |
| 6,193,754 B1 | 2/2001 | Seedhorn | |
| 6,235,057 B1 | 5/2001 | Roger et al. | |
| 6,306,138 B1 | 10/2001 | Clark et al. | |
| 6,599,289 B1 | 7/2003 | Bojarski et al. | |
| 6,641,395 B2 | 11/2003 | Kumar et al. | |
| 6,716,234 B2 | 4/2004 | Grafton et al. | |
| 6,886,569 B2 | 5/2005 | Chervitz et al. | |
| 7,246,976 B2 * | 7/2007 | Nordlin | B23B 51/0009 408/225 |
| 2003/0050666 A1 | 3/2003 | Grafton | |
| 2003/0065391 A1 | 4/2003 | Re et al. | |
| 2003/0130666 A1 | 7/2003 | Whittaker et al. | |
| 2004/0092936 A1 | 5/2004 | Miller et al. | |
| 2004/0199166 A1 * | 10/2004 | Schmieding | A61B 17/1617 606/79 |
| 2005/0084350 A1 * | 4/2005 | Nordlin | B23B 51/0009 408/225 |
| 2005/0273107 A1 * | 12/2005 | Stevens | A61B 17/1615 606/916 |
| 2006/0118341 A1 * | 6/2006 | Huber | B23B 51/02 175/420.1 |
| 2008/0319467 A1 * | 12/2008 | Wenchell | A61B 17/3496 606/170 |

FOREIGN PATENT DOCUMENTS

| | | |
|---|---|---|
| EP | 1 836 977 A1 | 9/2007 |
| WO | WO 2006/009471 A1 | 1/2006 |

OTHER PUBLICATIONS

Norseman Drill, "Drill Blanks," downloaded from http://www.norsemandrill.com/Twist_Drill_Term.html on Mar. 29, 2010.
Acufex catalog, Cruciate Reconstruction ACL Pins and Wires, Smith & Nephew Endoscopy, 1996 Products Catalog.

* cited by examiner

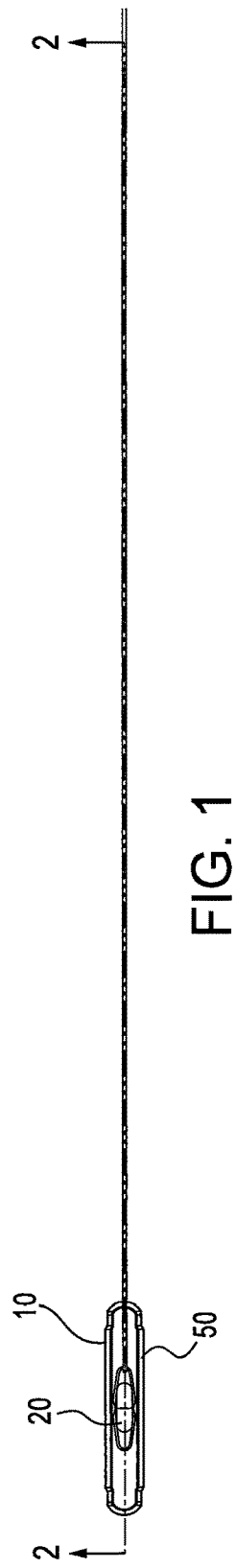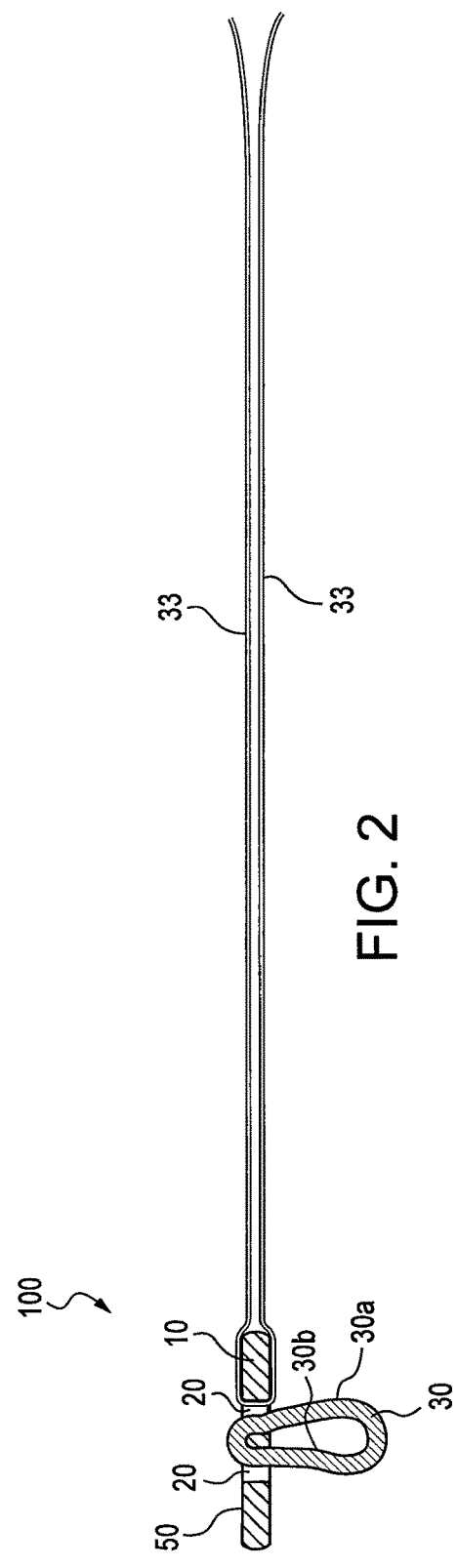

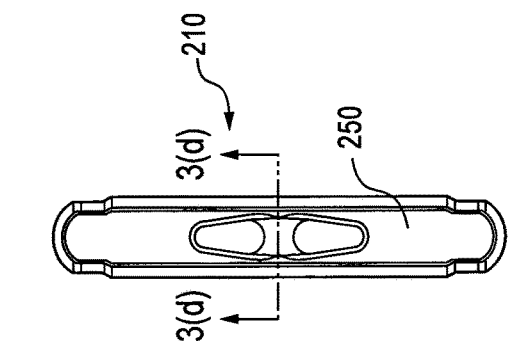
FIG. 3(a)
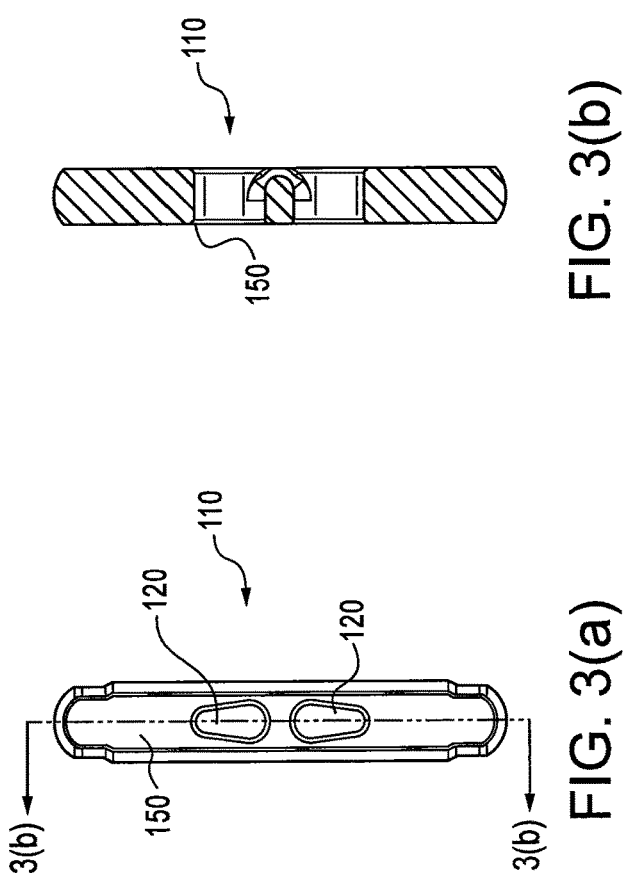
FIG. 3(b)
FIG. 3(c)
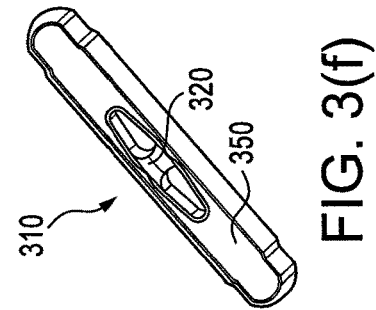
FIG. 3(d)
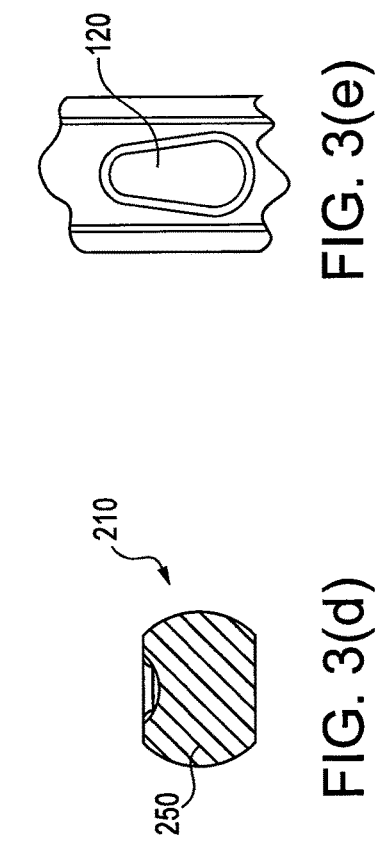
FIG. 3(e)
FIG. 3(f)

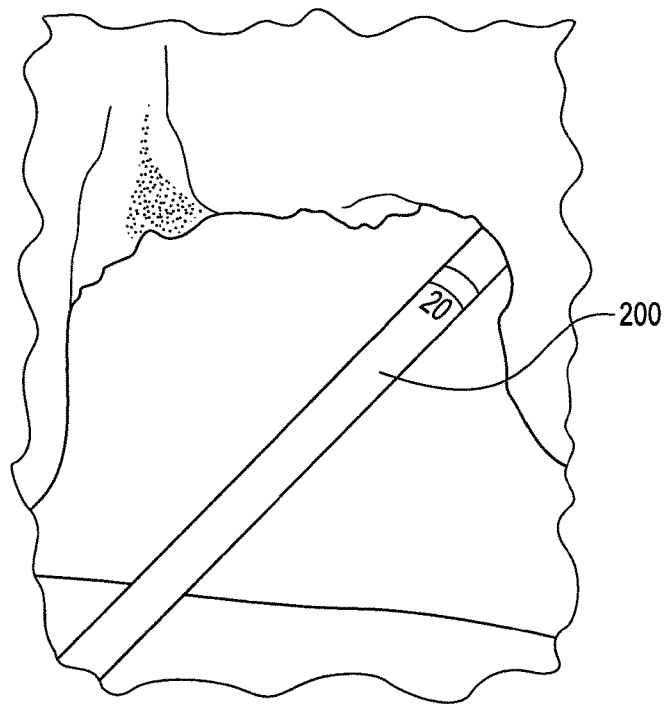
FIG. 19
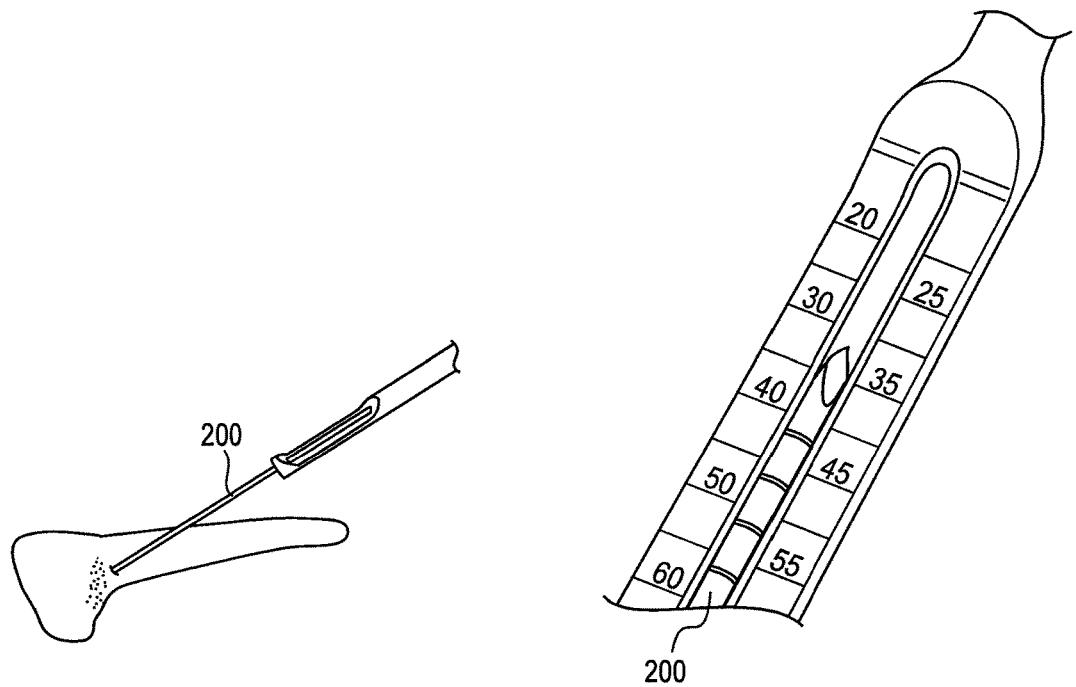
FIG. 20
FIG. 21

DRILL PIN FOR FIXATION OF LIGAMENTS USING BUTTON/LOOP CONSTRUCT

This application is a divisional of U.S. application Ser. No. 12/010,537, filed on Jan. 28, 2008, now U.S. Pat. No. 8,882,833, which claims priority to U.S. Provisional Application Ser. No. 60/897,230, filed on Jan. 25, 2007, and which is a continuation-in-part of U.S. application Ser. No. 11/889,740, filed on Aug. 16, 2007, which claims priority to U.S. Provisional Application Ser. No. 60/837,937, filed on Aug. 16, 2006.

FIELD OF THE INVENTION

The present invention relates to the field of surgery and, more particularly, to a drill pin for fixation of ligaments using a button/loop construct.

BACKGROUND OF THE INVENTION

Reconstructive surgeries, particularly anterior cruciate ligament (ACL) reconstruction, are well-known in the art. Methods of ACL reconstruction using interference screw fixation are described, for example, in U.S. Pat. Nos. 5,211,647 and 5,320,626. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like.

BRIEF SUMMARY OF THE INVENTION

The present invention provides a reconstruction system for ligament repair. More particularly, the present invention provides a drill pin for use with a button/loop construct for fixating a first tissue to a second tissue (for example, soft tissue to bone, or bone to bone). The drill pin includes a tip that widens out to cut a wider tunnel and to allow the button/loop construct to pass through it. The drill pin is also provided with a suture eyelet that is located at the proximal end of the pin and that captures suture attached to the button/loop construct. Preferably, the shaft of the drill pin is calibrated for bone depth. For example, the drill pin may be provided with marks, such as laser marks, to allow measurement of the distance from the femoral notch to the outer cortex, by itself or in conjunction with a depth guide, or the intraarticular space (between tibia and femur, for example, in transtibial ACL reconstruction).

The invention also provides a method of fixating a first tissue to a second tissue, for example, soft tissue to bone, by employing a button/loop construct in conjunction with the drill pin, the drill pin being configured to lead the button/loop construct through a bone tunnel, the drill pin having a suture eyelet for capturing sutures attached to the button/loop construct. An exemplary method of ACL reconstruction using the button/loop construct in conjunction with the drill pin includes, for example, the steps of: (i) drilling a femoral tunnel using a drill pin comprising a shaft of a first diameter, the shaft being provided with laser marks; a pin tip of a second diameter which is greater than the first diameter; and a eyelet; (ii) securing a button/loop construct with an attached graft (soft tissue graft or BTB graft) to the drill pin by passing suture from the button/loop construct through the eyelet in the drill pin; (iii) passing the drill pin and the suture/button construct with the attached graft through the femoral tunnel, with sutures from the suture loop/button construct being passed through the eyelet of the drill pin; and (iv) securing the button to the femoral cortex once the button exits the femoral socket.

The drill pin allows unmatched flexibility in femoral socket preparation for ligament reconstruction and the button/loop construct facilitates minimally invasive fixation in sockets that cannot be reached by straight screwdrivers or crosspin guides. Additionally, the method of ligament reconstruction of the present invention provide an alternative fixation technique that simplifies measuring during transtibial drilling and eliminates overdrilling of the cortex.

Other features and advantages of the present invention will become apparent from the following description of the invention which refers to the accompanying drawings.

BRIEF DESCRIPTION OF THE DRAWINGS

FIG. 1 illustrates a button/loop construct employing a button, according to the present invention;

FIG. 2 illustrates a cross-sectional view of the button/loop construct employing the button of FIG. 1, according to an embodiment of the present invention;

FIGS. 3(a)-3(f) illustrate various views of the button/loop construct of the present invention;

FIGS. 19-21 illustrate a method of ACL reconstruction employing the button/loop construct and the drill pin of the present invention, according to another embodiment of the present invention.

DETAILED DESCRIPTION OF THE INVENTION

Figure 4:
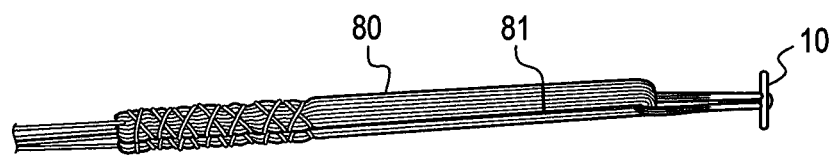
FIGS. 4-9 illustrate various steps of a method of ACL reconstruction employing the button/loop construct of the present invention, according to an embodiment of the present invention.
Figure 5:
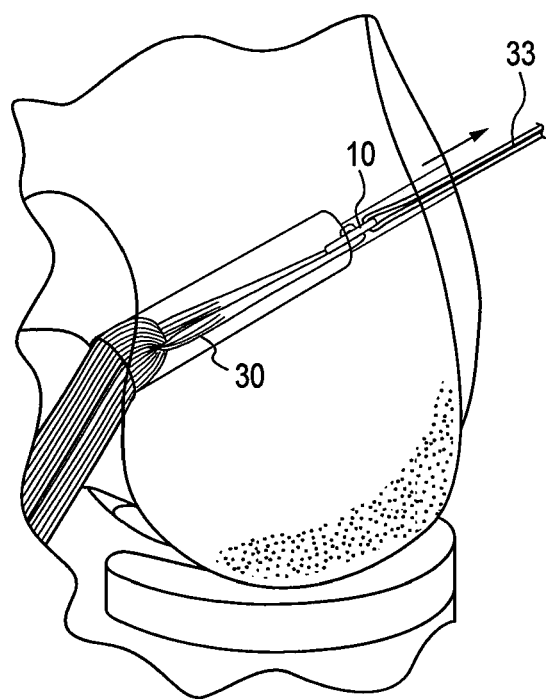
Figure 5A:
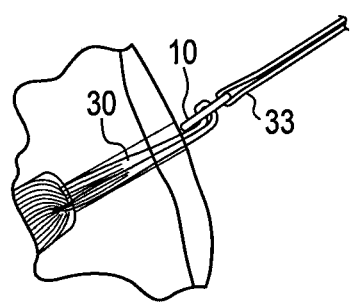
Figure 6:
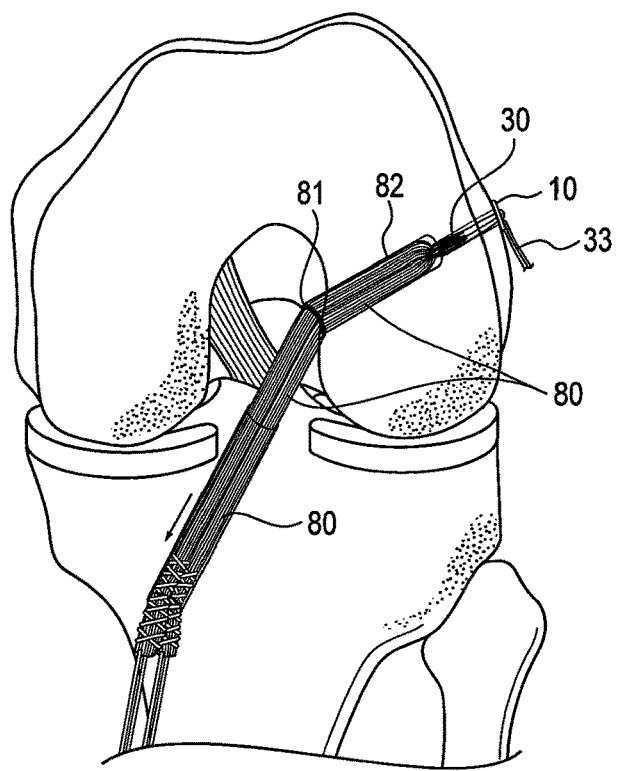
Figure 7:
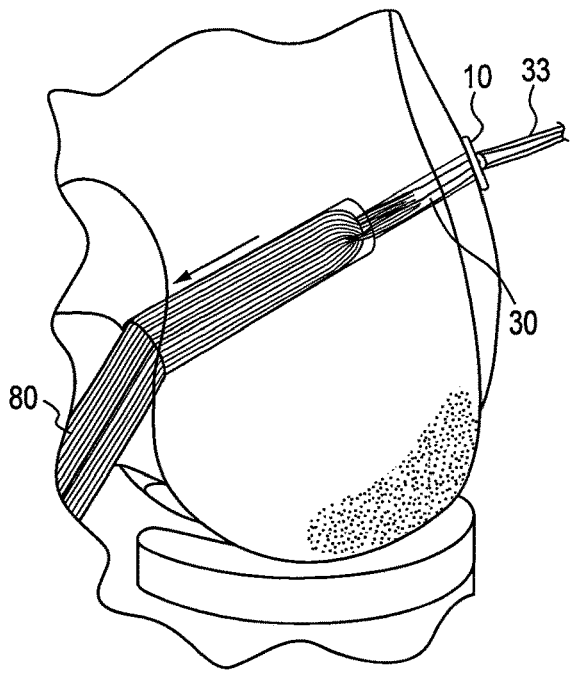
Figure 8:
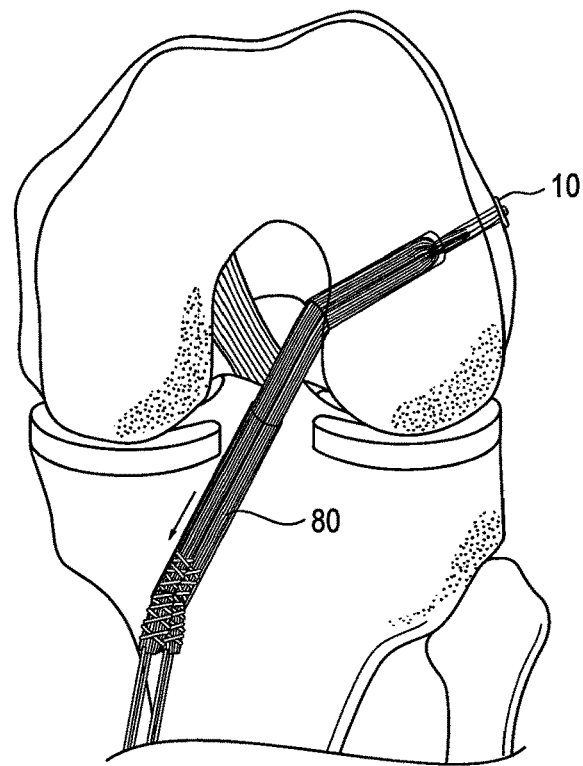
Figure 9:
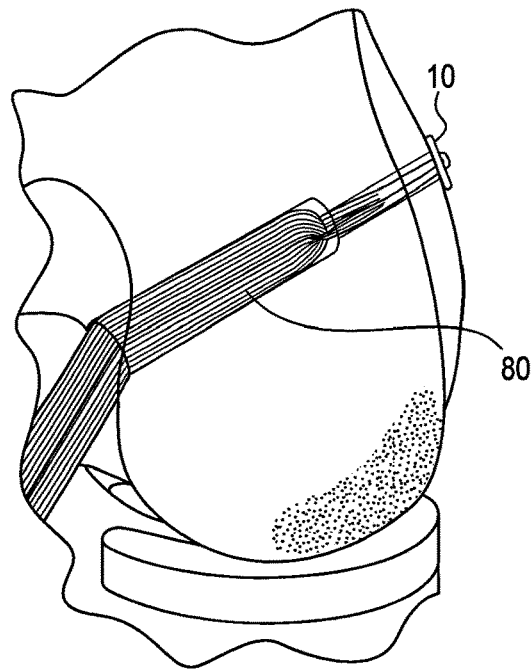

The present invention provides a technique and reconstruction system for ligament or tendon repair. The system of the present invention includes drill pin designed for use with a button/loop construct to achieve strong fixation on cortical bone. The drill pin includes a pin tip and/or a suture eyelet. The pin tip widens out to cut a wider tunnel and to allow the button/loop construct to pass through it and the suture eyelet is located at the proximal end of the pin to capture sutures attached to the button/loop construct.

Referring now to the drawings, where like elements are designated by like reference numerals, FIGS. 1-3(f) illustrate a button/loop construct 100 of the present invention provided with a button 10 and a continuous loop 30 attached to the button. As shown in the drawings, the button has an oblong configuration and a width that is preferably less than about 1 mm narrower than the width of the drill hole through which the button is inserted and subsequently passed through. The button is provided with an inside eyelet 20 that allows the passage of the continuous loop 30.

Preferably, button 10 has a length of about 10 mm to about 20 mm, more preferably of about 12 mm to about 15 mm, and a width that is less than about 1 mm narrower than the width of the drill hole through which the button is inserted and subsequently passed through. Preferably, button 10 is very small, having a width that allows it to pass through a 3 mm cortical pin hole without over drilling, which in turn saves time and preserves bone. Button 10 is made of, for example, a titanium alloy.

As shown in FIGS. 1-3(f), the button 10 is provided with an inside eyelet 20 having a specific configuration that allows the passage of a continuous loop 30, preferably a suture loop. In an exemplary embodiment, the suture loop 30 may be a single high strength suture such as a FiberWire® suture, sold by Arthrex, Inc. of Naples, Fla., and described in U.S. Pat. No. 6,716,234, the disclosure of which is incorporated by reference herein. The continuous suture loop may be available in various lengths and, preferably, is the equivalent of about three #5 FiberWire® suture strands, with a wide atraumatic graft interface to protect the graft integrity.

Figure 12:
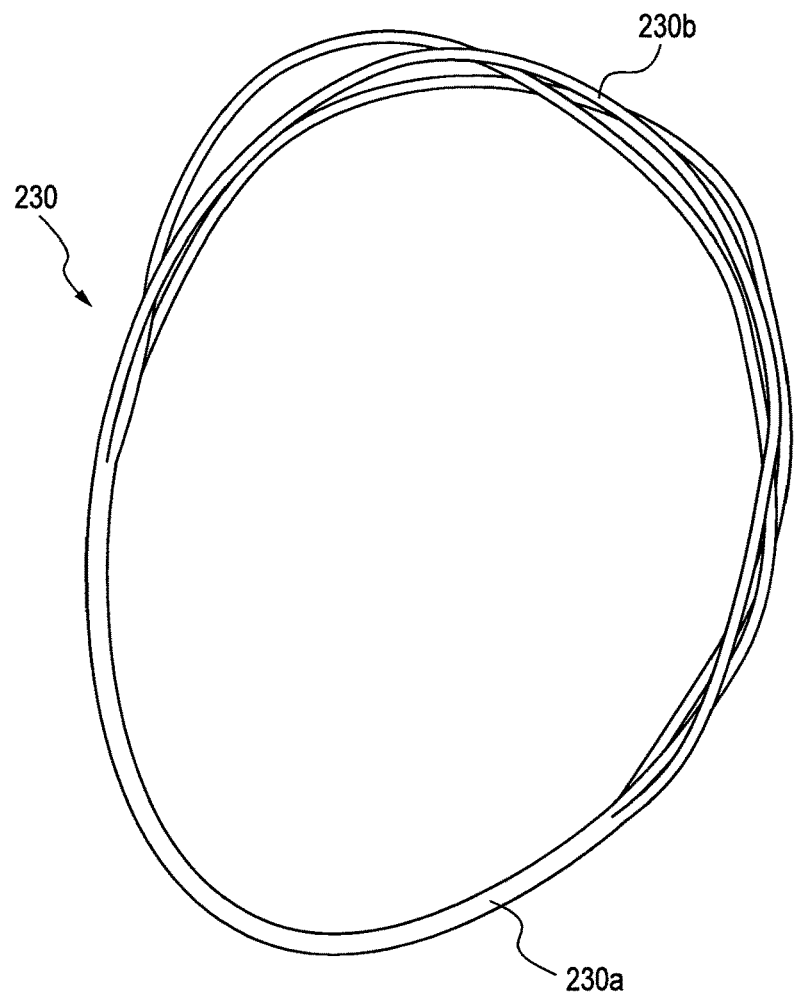
FIGS. 12 and 13 illustrate an embodiment of the continuous suture loop which transitions from one strand to three strands.
Figure 13:
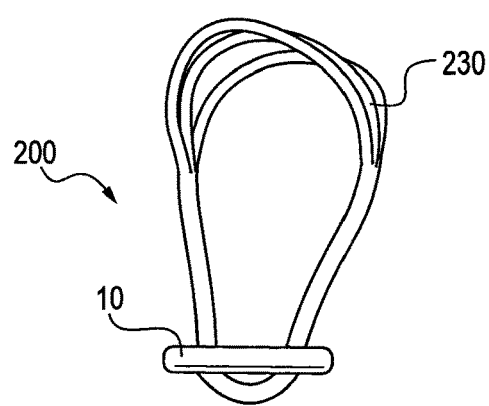
Figure 14A:
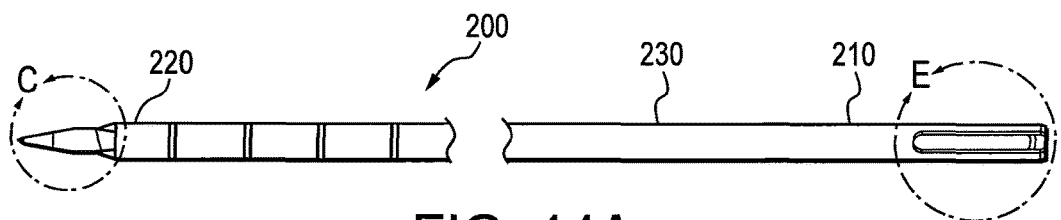
FIGS. 14A-16 illustrate a drill pin which may be employed with the button/loop construct of the present invention for ligament reconstruction.
Figure 14B:
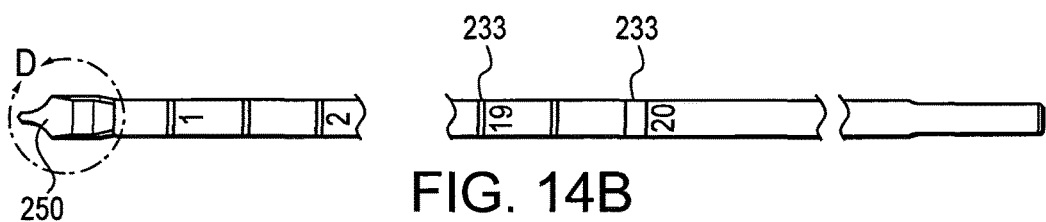
Figure 14C:
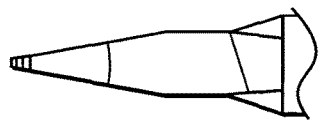
Figure 14D:
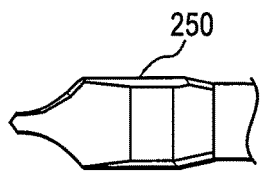
Figure 14E:
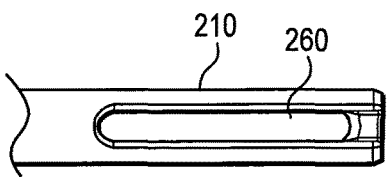
Figure 14F:
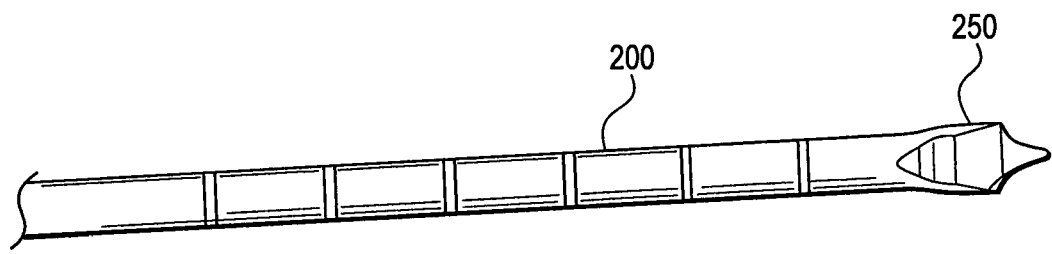
Figure 15:
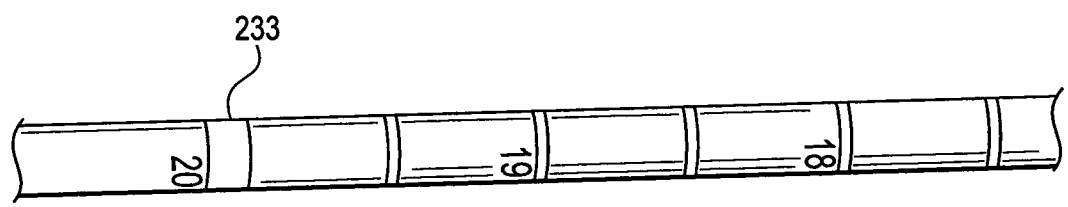

In another exemplary embodiment, the continuous loop 30 may be formed of a plurality of suture strands configured to separate from a single strand to a plurality of strands in a continuous loop. For example, the continuous loop 30 may include a braided strand of FiberWire® that is configured to trifurcate from one single strand to three strands (FIG. 12). In this exemplary "three strand" design, the continuous loop is configured to pass through the button component at the single strand section of the loop (FIG. 13).

The system of the present invention may be employed for fixation of bone-to-bone (BTB), or for fixation of soft tissue to bone. In an exemplary embodiment, the button/loop construct 100 of the present invention is used to secure a soft tissue graft in a bone socket in a retrograde manner, for example. According to another exemplary embodiment, the button/loop construct 100 of the present invention is used to secure a bone-to-bone (BTB) graft in a femoral tunnel or socket in a retrograde manner, for example.

In one embodiment of a method of ACL reconstruction using the button/loop construct 100 a femoral tunnel or socket is drilled using a retrodrill cutter which is inserted in a retrograde manner through the femur. A graft (soft tissue graft or BTB graft) is then secured to the button/loop construct 100 of the present invention. Subsequently, the graft with the button is passed through the femoral tunnel and the button is secured to the femoral cortex, once the button exits the femoral socket.

The exemplary technique of ACL reconstruction detailed above is further described below with reference to FIGS. 5-9, on soft tissue graft, and with reference to FIGS. 10 and 11, on BTB graft.

According to one embodiment of the present invention, a femoral socket is prepared by employing a retrodrill device provided with a retrodrill cutter detachable from a retrodrill guide pin, in the manner described in U.S. Patent Application Publication No. 2004/0199166, entitled "ACL Reconstruction Technique Using Retrodrill," the disclosure of which is hereby incorporated by reference herein in its entirety.

As described in U.S. Patent Application Publication No. 2004/0199166, a retrograde drill device for ACL reconstruction is provided with a cutter detachable from a guide pin. The cutter is inserted in a retrograde manner through the femur by employing a guide pin provided with depth markings. Once the proper anatomical position in the joint for creating a femoral socket has been located, the marking hook of a drill guide is placed through the antero-medial portal and inserted in an "over-the-top" position according to an outside-in technique. The guide pin is then inserted into the sleeve of the drill guide and drilled through the lateral femur until contact is made with a marking hook of the drill guide.

The cutter is then placed into the anatomical joint space through the antero-medial portal and positioned so that the guide pin can be threaded onto the cutter. Once secured within the cutter, the guide pin is retracted in a retrograde manner until the cutter contacts the femoral intercondylar notch. The proximal end of the guide pin is coupled to a drill. The cutter is then rotated and retracted into the lateral femur to the proper depth as measured on the outside of the knee by the depth markings on the guide pin. After the femoral socket is formed in this manner, the cutter is removed from the guide pin by applying a reversed drilling motion to the guide pin while grasping the cutter.

A tibial tunnel or socket may be formed, by the method described above or by a conventional method, before or after the formation of the femoral socket.

Once the femoral and tibial tunnels or sockets have been completed, graft insertion and fixation may be subsequently carried out. According to an exemplary embodiment of the present invention, and as illustrated in FIGS. 4-9, graft 80 which may be a soft tissue graft is folded in half over the loop 30 of the button 10 and tension is applied. A sterile marker may be employed to draw a line on the graft 80, the line indicating a distance that equals the length of the femoral socket or tunnel plus an additional length, measured from the looped end of the graft 80. For example, the additional length may be about 6 mm if using a 12 mm button, or about 8 mm if using a 15 mm button. This mark will be used to indicate when the button 10 has exited the femoral tunnel or socket.

Subsequently, passing sutures 33 are pulled and the graft 80 is passed into the femoral tunnel or socket. When the line marked on the graft 80 reaches the opening of the femoral socket or tunnel on the femoral cortex, a slight popping sensation may be felt as the button 10 exits and begins to flip horizontally on the femoral cortex. A distal traction on the graft 80 is applied and the passing sutures 33 are released to facilitate complete deployment of the button 10. The passing sutures 33 may be removed and tibial fixation may be completed.

Figure 11:
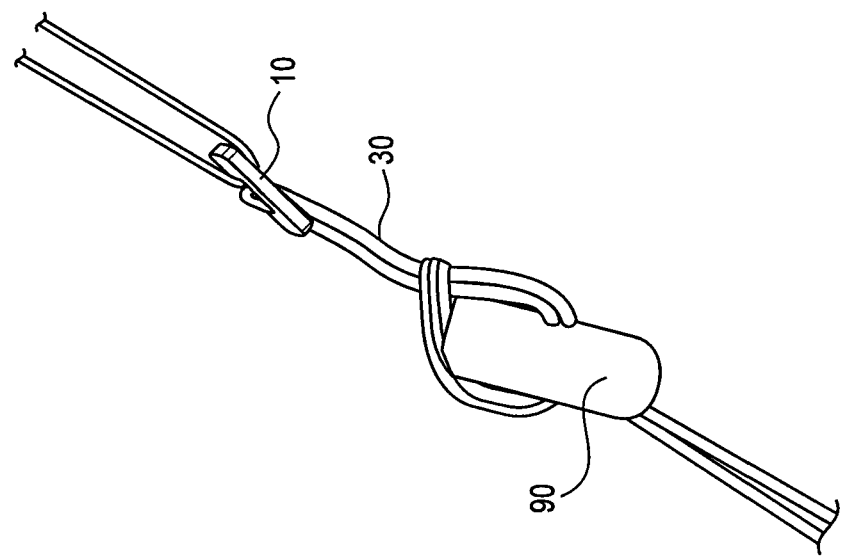
FIGS. 10 and 11 illustrate a button/loop construct of the present invention used for bone-to-bone (BTB) fixation, according to anther embodiment of the present invention.
Figure 10:
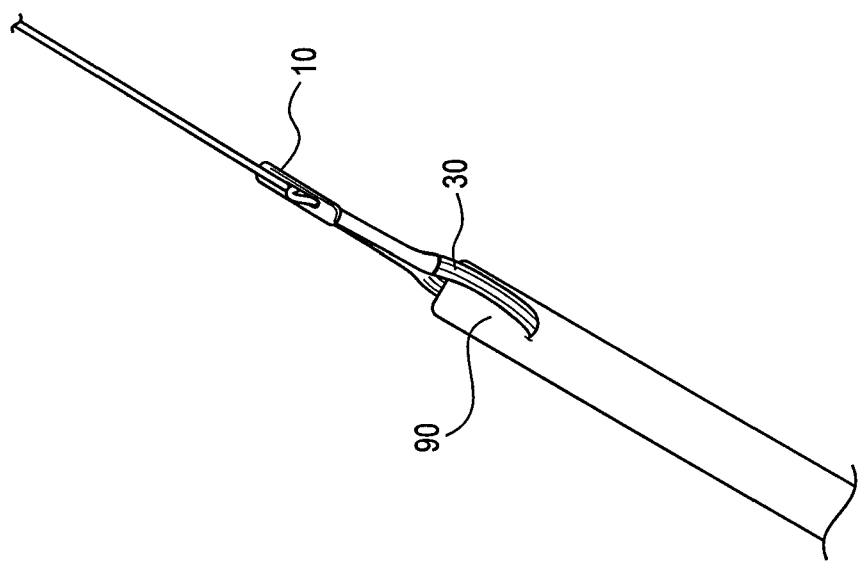

FIGS. 10 and 11 illustrate a BTB graft 90 which is secured within a femoral tunnel by employing the button/loop construct 100 of the present invention. BTB graft 90 is secured within the femoral tunnel in a manner similar to that described above with reference to the soft tissue graft 80. The femoral tunnel is formed preferably in a retrograde manner and the button/loop construct 100 is also preferably inserted in a retrograde manner.

Reference is now made to FIGS. 14A-16 which illustrate a drill pin 200 of the present invention and which is configured to be used with the button/loop construct 100 (described above) for fixating a first tissue to a second tissue (for example, soft tissue to bone). As shown in FIGS. 14A-16, the drill pin 200 includes a shaft 230, a proximal end 210 and a distal end 220. A pin tip 250 is provided at the distal end 220. The pin tip 250 has a width greater than the diameter of the shaft 230. For example, if the pin shaft diameter is 2.4 mm, which allows its use with transtibial ACL guides and cannulated reamers, the pin tip may widen out to cut a wider tunnel, for example, a 3 mm tunnel, to allow the button/loop construct 100 to pass through it.

The shaft 230 of the drill pin 200 is preferably calibrated for bone depth. In an exemplary embodiment, the shaft 230 is provided with a plurality of marks 233, preferably laser marks, for measuring the distance from the femoral notch to the outer cortex by itself, or in conjunction with a depth guide. The marks 233 may be additionally used to measure the intraarticular space, from tibia to femur, for transtibial ACL reconstruction. In this manner, the marks 233 simplify measuring by allowing the surgeon to measure right off the drill pin 200 during drilling or with the depth guide.

Figure 16:
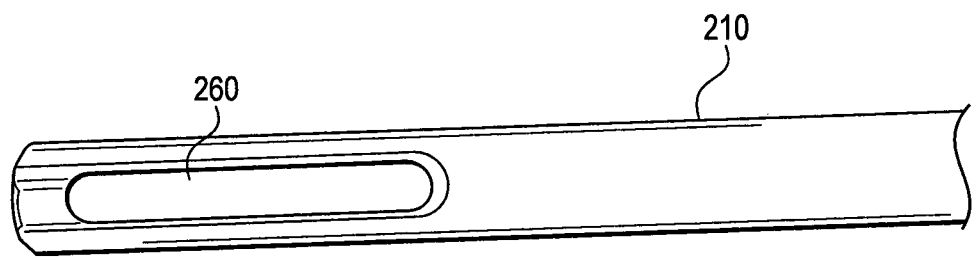

As illustrated in FIG. 16, drill pin 200 is also provided with a suture eyelet 260 that is located at the proximal end 210 of the drill pin. The suture eyelet 260 allows sutures from the button/loop construct 100 and graft 80, 90 attached thereto to pass through the suture eyelet 260 and through the knee.

TABLE 1

Drill pin

| | |
|---|---|
| Dimensions: | 406 mm (overall length), 2.4 mm (diameter) |
| Material: | Stainless steel with electropolish finish; titanium alloy |
| Markings: | Laser mark graduated laser lines along the length, all markings within 200 mm from the distal end |
| Eyelet: | 1.0 mm (width), 1.50 mm from proximal end, 8.4 mm (length) |
| Tip: | 6.3 mm (length), 120° relief angle for all cutting surfaces which are 180° opposed, 2.75 mm (diameter at radial relief), 3 mm (diameter at cutting edge) |

Distance and depth measuring techniques using the drill pin 200 described above are illustrated with reference to FIGS. 17 and 18 (option 1) and FIGS. 19-21 (option 2).

Figure 17:
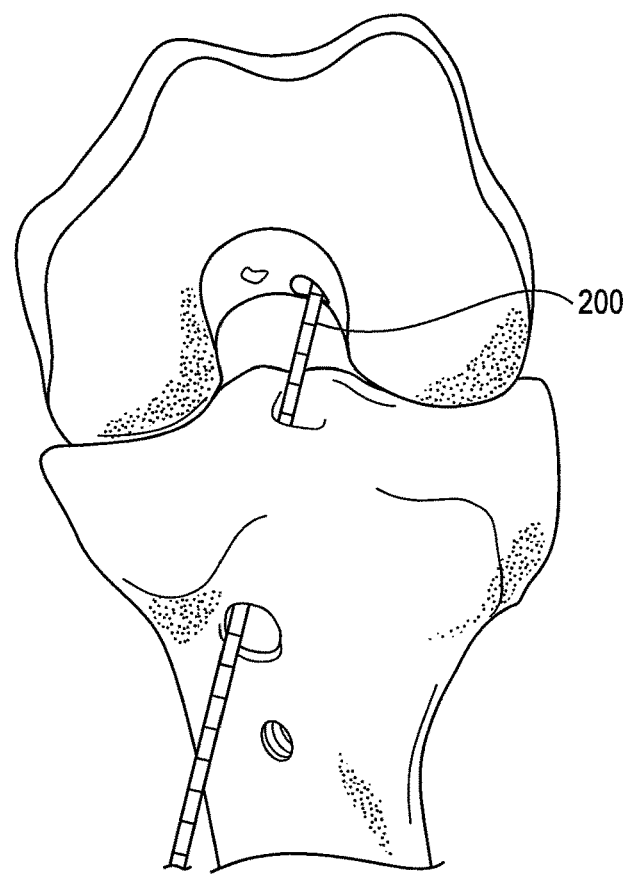
FIGS. 17 and 18 illustrate a method of ACL reconstruction employing the button/loop construct and the drill pin of the present invention, according to an embodiment of the present invention.
Figure 18:
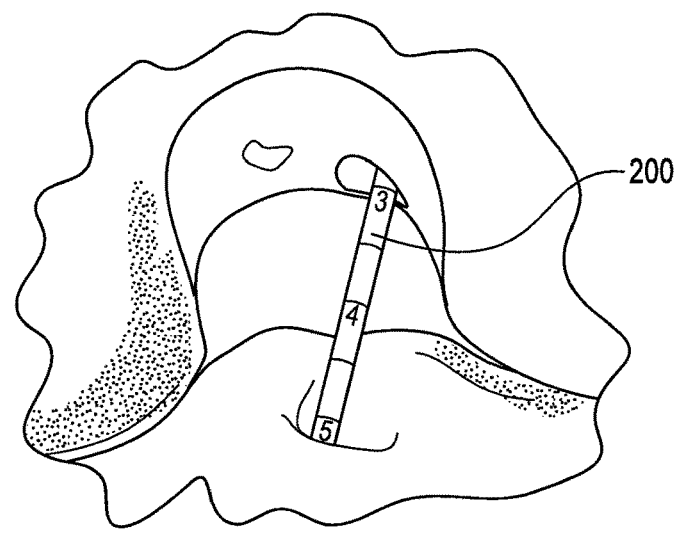

Referring to FIGS. 17 and 18, the drill pin 200 is drilled through femur until the outer cortex is drilled, at which point a distinctive tactile sensation may be felt due to the transitioning from soft (cancellous) bone to hard (cortical) bone. When this is felt, the depth marking against the femoral notch (FIG. 18) is noted. In a particularly exemplary embodiment, the marking should read about 3 cm. Subsequently, a cannulated reamer is placed over the drill pin 200 to drill the femoral socket.

Referring to FIGS. 19-21 (option 2), the drill pin 200 is drilled until the "20" mark (a thick laser line) is even with the opening of the femoral socket. A depth guide such as a Retrobutton depth guide is then placed over the drill pin 200 and pushed down the bone (FIG. 20). The length of the bone from the femoral notch to the cortex is read where the pin tip meets the guide. In a particularly exemplary embodiment, this length is about 32 mm.

FIGS. 22-29 illustrate additional embodiments for the preparation and measurement of the femoral socket using the drill pin 200 and for the passing of a graft (such as graft 80, 90) through the tunnel with the button/loop construct 100 of the present invention.

Figure 22:
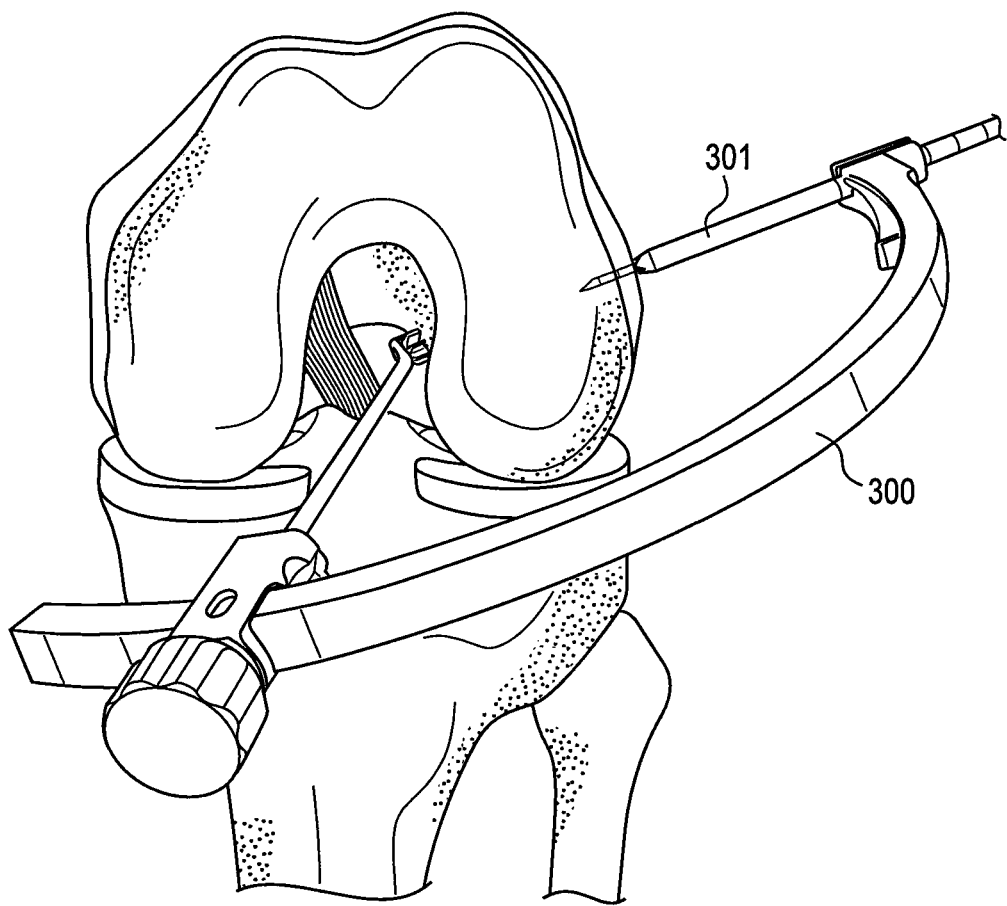
FIGS. 22-29C illustrate additional methods of ACL reconstruction employing the button/loop construct and the drill pin of the present invention, according to additional embodiments of the present invention.
Figure 23A:
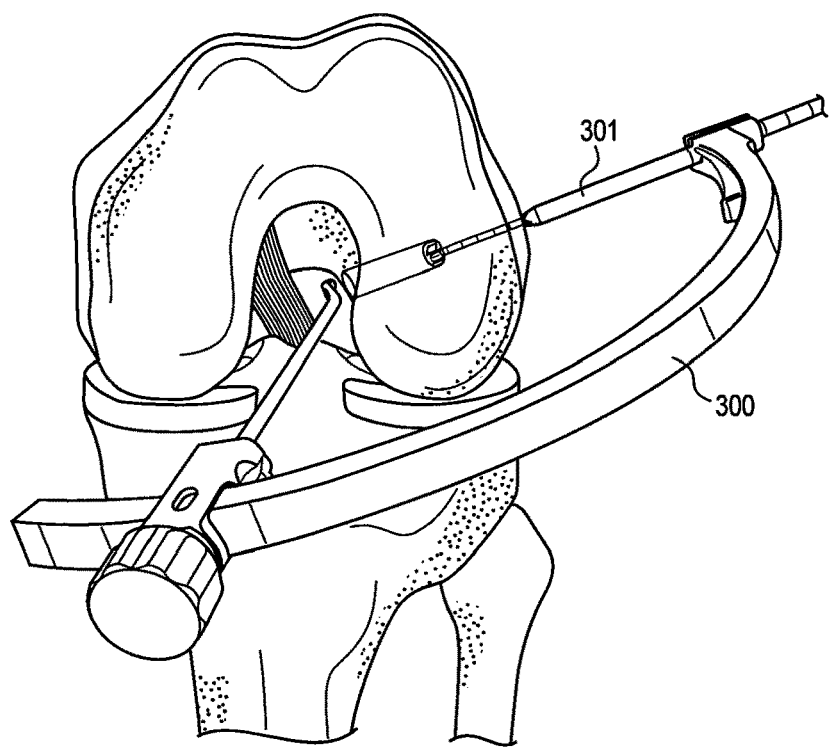
Figure 23B:
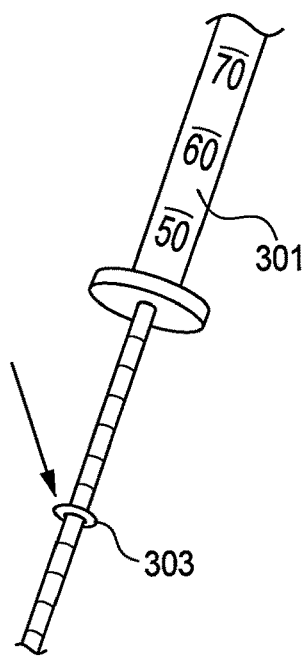
Figure 23C:
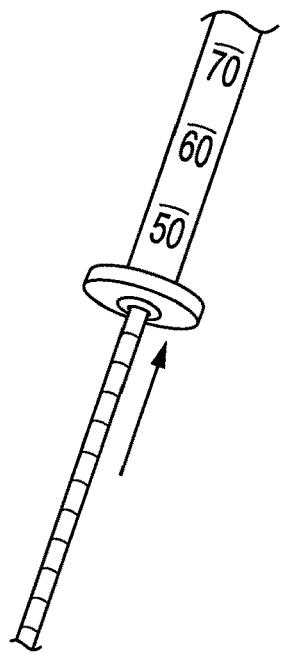
Figure 24A:
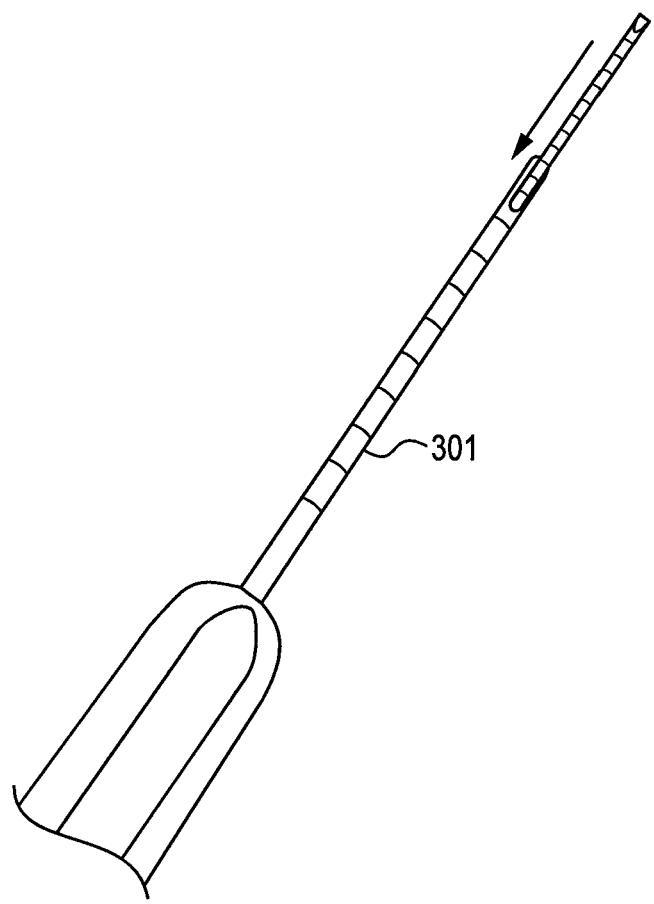
Figure 24B:
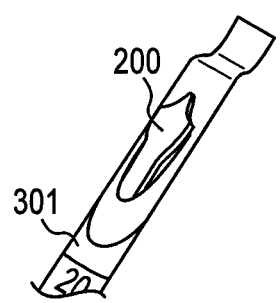
Figure 25A:
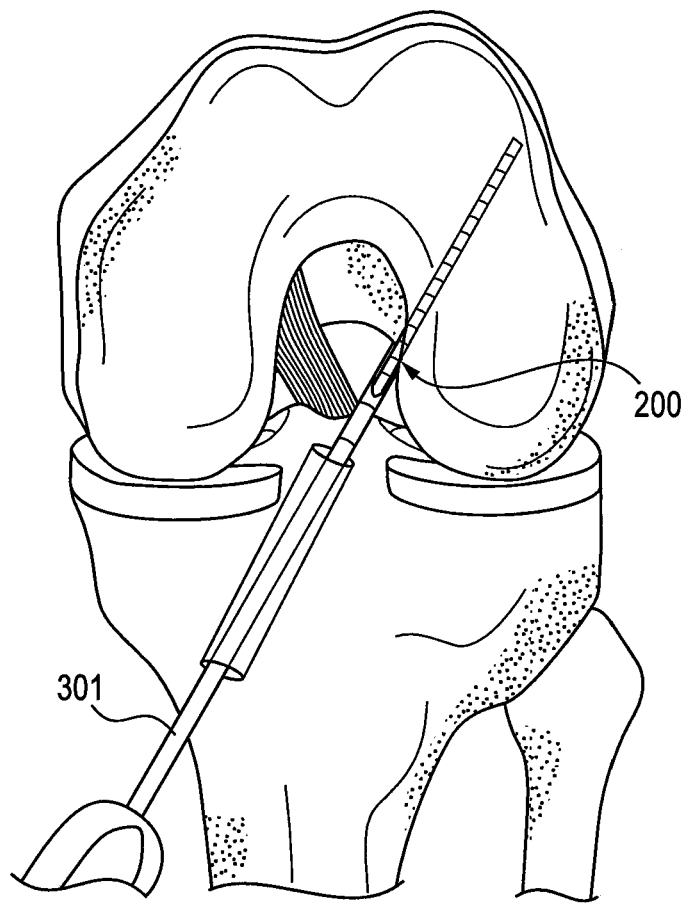
Figure 25B:
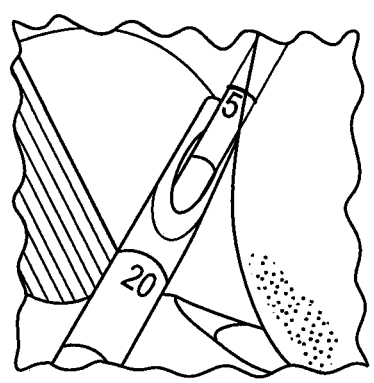

Reference is now made to FIGS. 22-23C and FIGS. 24A-27C, which illustrate two options for the formation and measurement of the femoral socket in accordance with embodiments of the present invention: the RetroDrill™ Technique (FIGS. 22-23C) and the Transtibial Femoral Preparation (FIGS. 24A-27B). As shown in FIG. 22, a femoral guide 300 is placed into the knee. A drill guide sleeve 301 is pushed to bone before retrodrilling, noting the transosseous length on the retrodrill sleeve. The drill pin 200 is then drilled into the joint and engages the retrocutter. As shown in FIG. 23B, the rubber ring 303 is set to the end of the guide sleeve 301. The socket is created by drilling on forward and pulling the drill back, away from the bone. The depth of the socket is read by counting the 5 mm laser line marks between the guide sleeve 301 and the rubber ring 303.

FIGS. 24A-27B illustrate the second option for the formation and measurement of the femoral socket in accordance with the present invention. The drill pin 200 is preloaded into a transtibial femoral ACL drill guide by placing the end of the drill pin 200 through the cannulated tip (inset of FIG. 24). The drill pin 200 has a spade tip that rests above the cannulation of the guide sleeve 301 (FIG. 24B). The guide sleeve 301 is inserted into the knee through the tibial tunnel and the tip is placed in "over the top" position. Alternatively, the guide sleeve 301 may be placed through the anteromedial portal. The drill pin 200 is then advanced into the femur until the lateral cortex is felt. The intraosseous length is measured by reading the measurement on the drill pin 200 closest to the femoral notch (FIG. 25B).

Figure 26A:
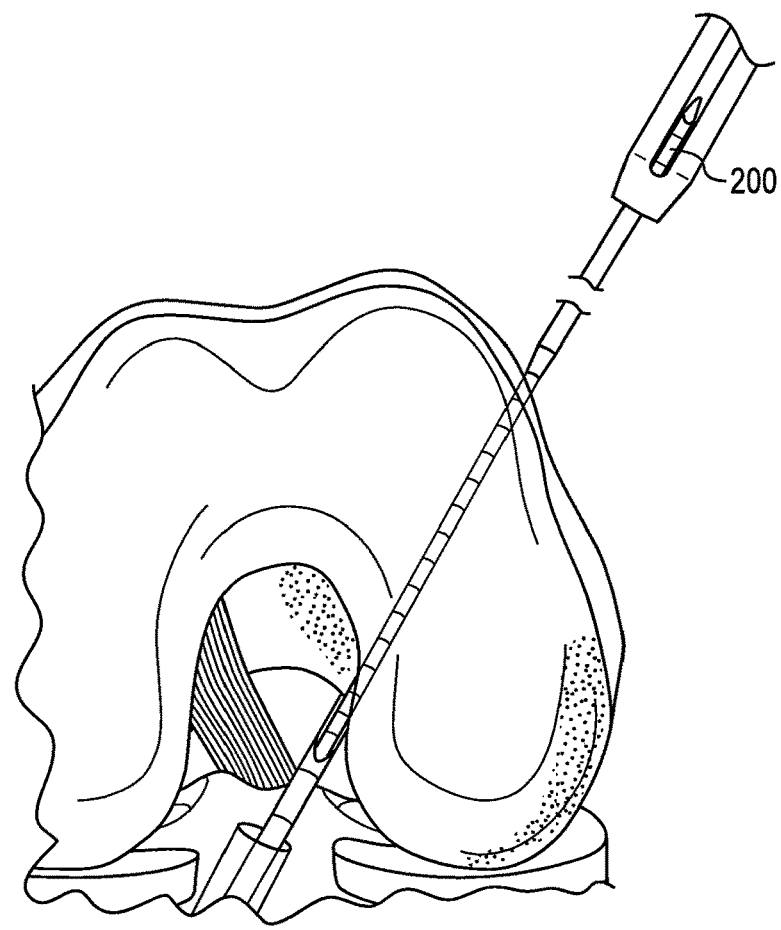
Figure 26B:
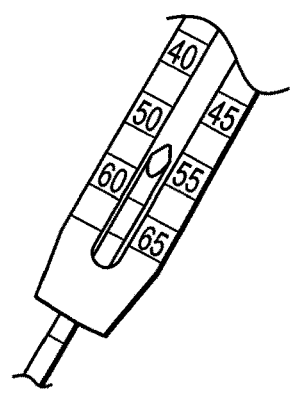
Figure 27A:
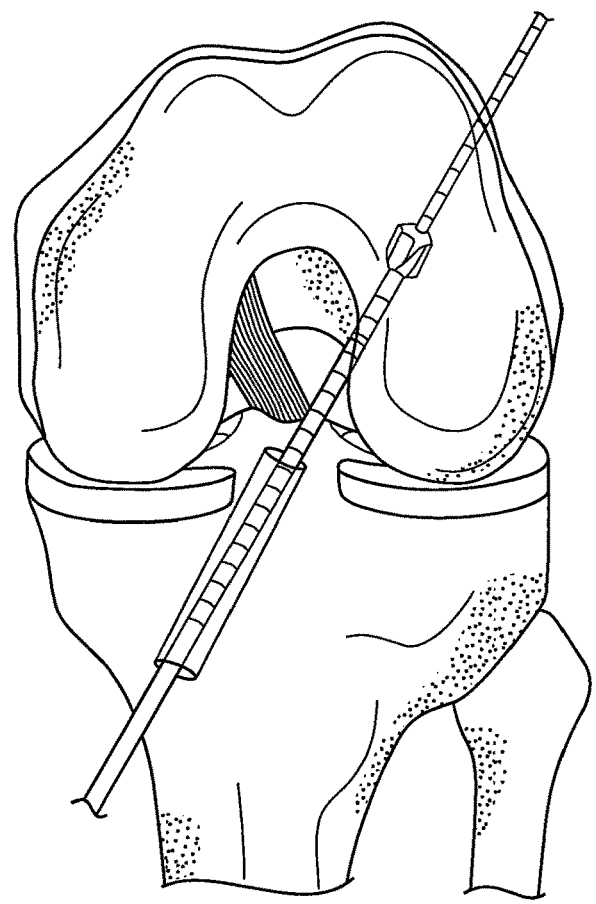
Figure 27B:
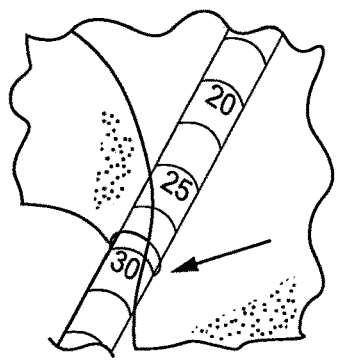

Alternatively, referring to FIG. 26A, the drill pin 200 is drilled to the 20 mm mark and the guide sleeve 301 is placed over the tip of the drill pin 200 and advanced to bone. The intraosseous length is measured by reading where the tip of the drill pin 200 ends on the guide sleeve 301 (FIG. 26B). A cannulated headed reamer is then placed over the drill pin 200 (FIG. 27A) and the femoral socket is drilled to a desired length, preferably about 30 mm (FIG. 27B).

Figure 28A:
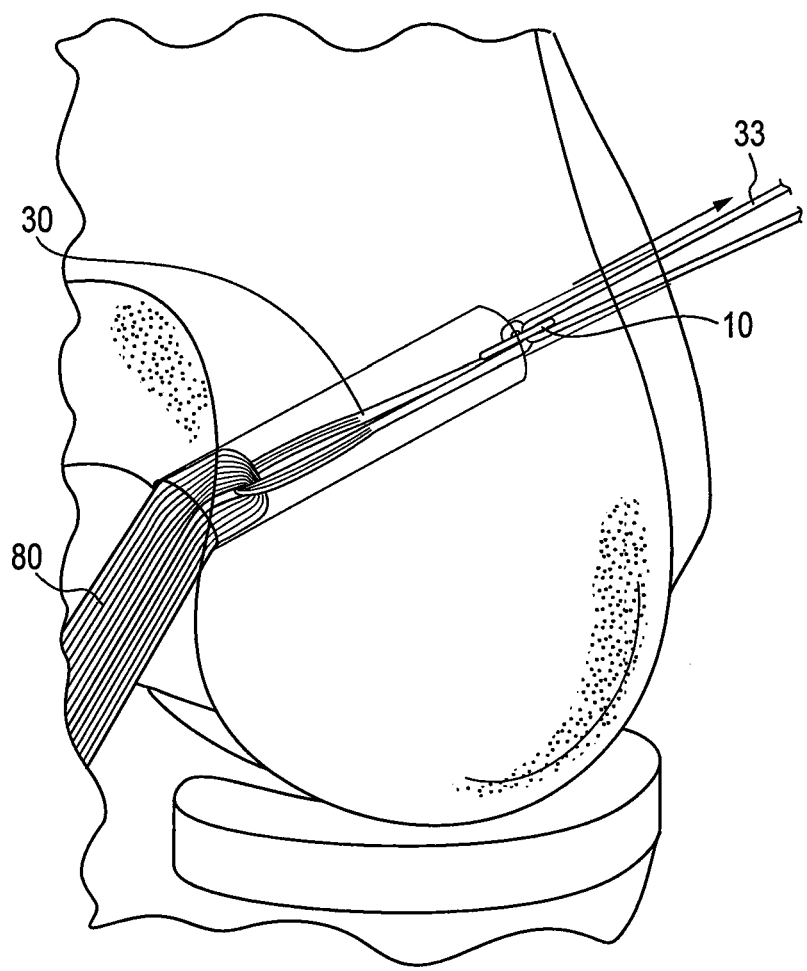
Figure 28B:
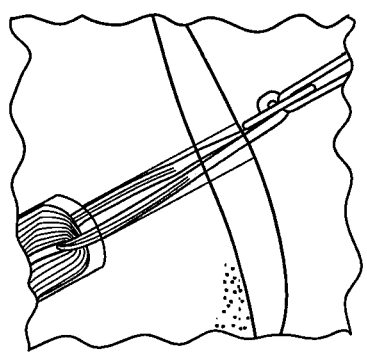
Figure 29A:
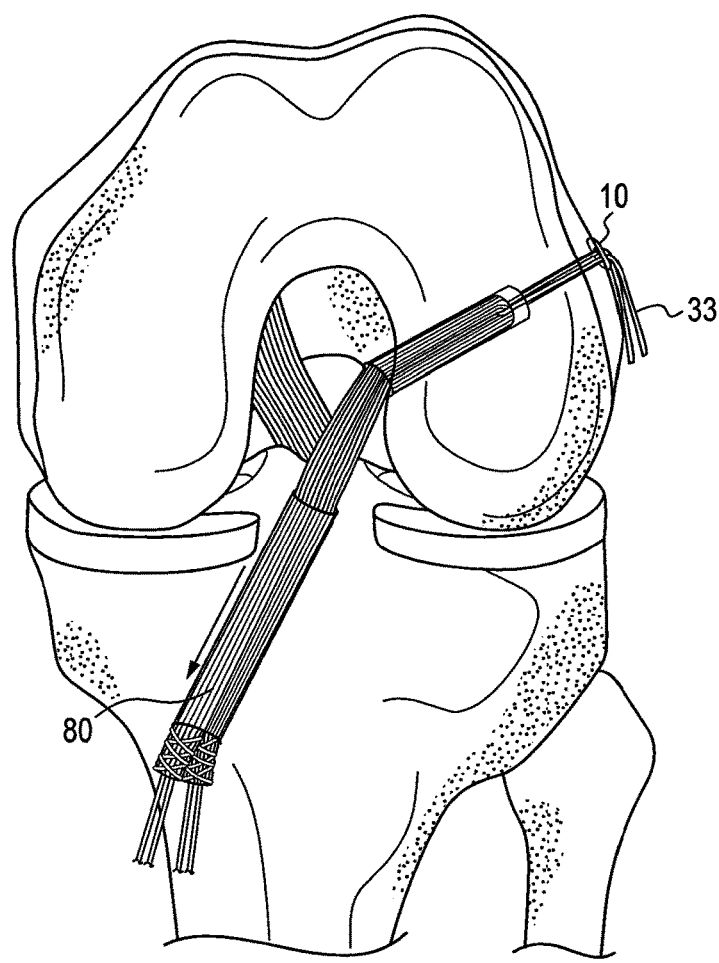
Figure 29B:
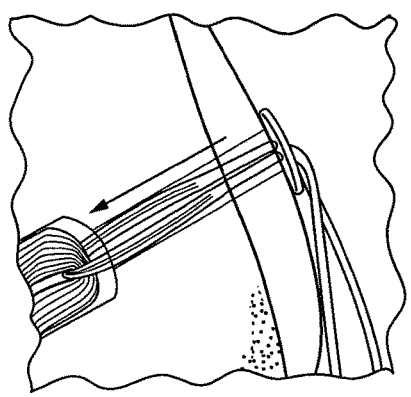
Figure 29C:
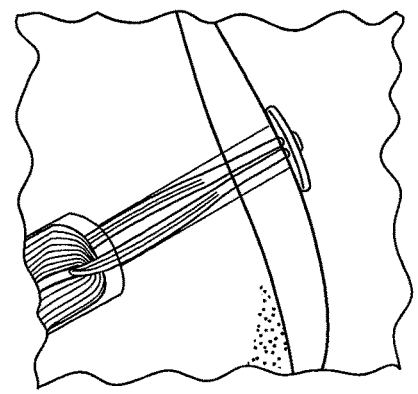

FIGS. 28A and 28B and FIGS. 29A, 29B and 29C, illustrate the graft passing for femoral fixation. As shown in FIG. 28A, passing sutures 33 are pulled and the graft 80 is passed into the femoral socket. When the line on the graft 80 reaches the orifice of the femoral socket, a slight "popping" sensation may be felt as the button 10 exits the femoral cortex and begins to flip horizontally. A distal traction is applied on the graft 80 and the passing sutures 33 are released to facilitate complete deployment of the button 10 (FIGS. 29A and 29B). The passing sutures 33 may be removed and tibial fixation completed.

Although the present invention has been described in relation to particular embodiments thereof, many other variations and modifications and other uses will become apparent to those skilled in the art.

What is claimed is:

1. A drill pin, comprising:
   a solid shaft extending along a longitudinal axis between a proximal end and a distal end;
   a plurality of laser marks formed on an external surface of the solid shaft;
   a suture eyelet located at the proximal end; and
   a pin tip located at the distal end and including a width that is greater than the solid shaft,
   wherein the pin tip gradually widens out and is adapted for cutting a tunnel in bone that is wider than the solid shaft,
   wherein the pin tip is spade-shaped,
   wherein the pin tip includes cutting surfaces that are 180° opposed.

2. The drill pin as recited in claim 1, wherein the suture eyelet includes an elongated opening formed through the proximal end.

3. The drill pin as recited in claim 1, wherein the drill pin is made of a metallic material and includes an electropolish finish.

4. The drill pin as recited in claim 3, wherein the metallic material includes a stainless steel or a titanium alloy.

5. The drill pin as recited in claim 1, wherein the plurality of laser marks are spaced at a predetermined length from the distal end.

6. The drill pin as recited in claim 1, wherein the cutting surfaces each include a relief angle of 120°.

7. The drill pin as recited in claim 1, wherein a diameter of the solid shaft is about 2.4 mm and the pin tip widens to about 3 mm.

8. The drill pin as recited in claim 1, wherein the pin tip is configured to engage a drill bit that is separate from the drill pin.

9. The drill pin as recited in claim 1, wherein the drill pin is part of a reconstruction system that includes a cannulated reamer.

10. The drill pin as recited in claim 9, wherein the cannulated reamer is receivable over the solid shaft of the drill pin.

11. The drill pin as recited in claim 1, wherein the pin tip includes first portions tapering outwardly from the solid shaft, second portions extending longitudinally and substantially parallel to the longitudinal axis, and third portions that are concave and taper inwardly before joining together at an apex of the pin tip.

12. The drill pin as recited in claim 11, wherein distal sections of the third portions connect to the apex and are located distally of proximal sections of the third portions that connect to the second portions.

13. The drill pin as recited in claim 1, wherein each of the plurality of laser marks are located within a distance from the distal end that is less than half of a total length of the drill pin.

14. The drill pin as recited in claim 1, wherein a diameter at a cutting edge of the pin tip is about 3 mm.

15. The drill pin as recited in claim 1, wherein a length of the pin tip is less than about 2% of a total length of the drill pin.

16. A drill pin, comprising:
a solid shaft extending along a longitudinal axis between a proximal end and a distal end;
a plurality of laser marks formed on an external surface of the solid shaft;
a suture eyelet located at the proximal end; and
a pin tip located at the distal end and including a width that is greater than the solid shaft,
wherein the pin tip gradually widens out and is adapted for cutting a tunnel in bone that is wider than the solid shaft,
wherein the pin tip is spade-shaped,
wherein the pin tip includes cutting surfaces that are 180° opposed,
wherein a length of the suture eyelet is about 2% of a total length of the drill pin.

17. A drill pin, comprising:
a solid shaft extending along a longitudinal axis between a proximal end and a distal end;
a plurality of laser marks formed on an external surface of the solid shaft;
a suture eyelet located at the proximal end; and
a pin tip located at the distal end and including a width that is greater than the solid shaft,
wherein the pin tip gradually widens out and is adapted for cutting a tunnel in bone that is wider than the solid shaft,
wherein the pin tip is spade-shaped,
wherein the pin tip includes cutting surfaces that are 180° opposed,
wherein the pin tip includes a first length that is less than a second length of the suture eyelet.

* * * * *